(12) United States Patent
Anastassiadis et al.

(10) Patent No.: US 6,303,351 B1
(45) Date of Patent: Oct. 16, 2001

(54) PROCESS FOR THE CONTINUOUS PRODUCTION OF CITRIC ACID BY FERMENTATION

(75) Inventors: Savas Anastassiadis, Artillerlestrasse 64, 52428 Jüllich (DE); Alexander Aivasidis; Christian Wandrey, both of Jüllich (DE)

(73) Assignee: Savas Anastassiadis, Somerville, MA (US)

( * ) Notice: Subject to any disclaimer, the term of this patent is extended or adjusted under 35 U.S.C. 154(b) by 0 days.

(21) Appl. No.: 08/208,123

(22) Filed: Mar. 8, 1994

(30) Foreign Application Priority Data

Mar. 10, 1993 (DE) ................................. 43 07 517

(51) Int. Cl.$^7$ ....................................... C12N 7/44
(52) U.S. Cl. ........................ 435/144; 435/135; 435/142
(58) Field of Search ................... 435/144, 142, 435/135, 921, 922, 923, 924

(56) References Cited

U.S. PATENT DOCUMENTS

| | | | |
|---|---|---|---|
| 3,902,965 | * 9/1975 | Furukawa et al. | 435/144 |
| 3,926,724 | * 12/1975 | Takayama et al. | 435/144 |
| 4,014,742 | * 3/1977 | Nubel | 435/144 |
| 4,278,764 | 7/1981 | Rottigni et al. | 435/144 |
| 4,322,498 | * 3/1982 | Takayama et al. | 435/144 |
| 4,389,484 | * 6/1983 | Tabuchi et al. | 435/144 |
| 4,391,908 | * 7/1983 | Tabuchi et al. | 435/144 |

FOREIGN PATENT DOCUMENTS 232 309 A1 1/1986 (DE) .
275 480 A1 1/1990 (DE) .

OTHER PUBLICATIONS

Parente et al. *Ann Microbiol. Enzimol* (1993) 43(1) 103–14.
El–Sang et al. *Ann Agric Science* (Cairo) 31 (2) 1986. p 965–988.
P.E.Milsom; "Organic Acids by Fermentation, Especially Citric Acid"; Food Biotechnology, vol. 1, 1987, p. 273 & 291.
Lewis B. Lockwood; "Production of Organic Acids by Fermentation"; Microbial Technology vol. I, pp. 355 & 363.
T.K.Klasson et al; "Continuous Fermentation for the Production of Acid from Glucose"; Applied Biochem & Biotech.. vol. 20/2189, p. 491–509.
Mitsui Sekiyu Kagaku Kogyo K.K.; "Production of Citric Acid"; 58–13838 C–194 Nov. 9, 1983 vol. 7 /No. 252, 2 pages.

* cited by examiner

*Primary Examiner*—Leon B. Lankford, Jr.
(74) *Attorney, Agent, or Firm*—Herbert Dubno; Jonathan Myers

(57) ABSTRACT

A process for producing citric acid/citrate for use in producing citric acid, comprising the steps of continuously feeding to a fermenter containing a yeast capable of transforming glucose to citric acid by fermentation, in the presence of a nutrient medium and oxygen, sugar, especially glucose as a C source and at least one ammoniun compound as an N source fermenting the sugar to citric acid in said fermenter at a temperature, a pH and with a residence time sufficient to transform at least a major part of the sugar continuously fed to said fermenter to citric acid continuously withdrawing fermentation product from said fermenter recovering citric acid/citrate from said fermentation product controlling a C/N ratio fed to said fermenter to correspond to a molar ratio of glucose to ammonium compounds of 12 to 22 during fermentation of the glucose to citrate.

15 Claims, 9 Drawing Sheets

PROCESS FOR THE CONTINUOUS PRODUCTION OF CITRIC ACID BY FERMENTATION

FIELD OF THE INVENTION

The present invention relates to a process for the continuous production of citric acid by fermentation with the aid of yeast.

BACKGROUND OF THE INVENTION citric acid, an aliphatic hydroxy acid, has been known as a natural fruit acid since the last century.

In nature, it is widely present as the acid and in the form of its salts and can be found in fruit, vegetables, milk and meat.

It is widely used in foods and beverages, in the pharmaceutical industry and for purification process and as an antioxidant so that commercial preparation independent of natural sources is necessary.

Citric acid has been long made from sugar or molasses by a fermentation process utilizing molds of the genus Aspergillus by the surface process and since the middle of this century by a submerged process.

Both processes are batch operations which can achieve yields between 57 to 77% within 1 to 2 weeks.

Since 1960, predominantly in Japan, citric acid has been produced utilizing other microorganisms, especially of the genus Candida, on other substrates of which n-alkanes are the most prominent.

In the Japanese Patent Publication J-58-138387, a process for producing citric acid from n-alkanes is described in which yeast strains of Candida or Saccharomycopsis are used to carry out fermentation in an agitated oxygen-aerated two-phase system where the optimum conversion is achieved with oxygen saturation values of 10 to 45%. The citric acid which is formed is isolated after interruption of the agitation by a phase separation from the aqueous phase which can be replenished a number of times. In this manner, citric acid yields up to 44 g/l can be obtained. Particulars with respect to the formation of isocitric acid are not available. A commercial production by this process is unknown.

In recent years, investigations into citric acid production has concentrated on the use of sugar containing media.

In the East German Patent Document 248,376, for example, citric acid is recovered in a batch process in which initially yeast (Yarrowinia lipolytica) is cultured upon a nutrient medium containing n-alkanes or substances with long $CH_2$ chains with addition of the customary mineral and trace element salt solutions until the N source has been consumed, sugar (125 g/l glucose or invert sugar) being Added and being transformed 90% to citric acid with 5% to isocitric avid. In this batch process significant problems arise with respect to the handling of the residual solution.

A continuous citrate production which would be favorable on economic grounds has not been industrially performed heretofore; on the contrary doubts about the utility of such a process have been repeatedly expressed (H. J. Peppler et. al. "Microbial Technology" Vol. I, Page 363, Acad. Press., London (1979); P. E. Milsom, "Food Biotechnology" Vol. I (1987) Page 291).

T. K. Klasson et al. (Appl. Biochem. Biotechnol. Vol. 20/21 (1989) Pages 491–509) have reported on comparative tests with continuous and bathwise production of citric acid by fermentation with yeast (Candida lipolytica). The continuous fermentation is carried in a single fermentor with a maximum residence time of 30 hours and >50% air saturation with glucose content (in the feed) of 30 to 150 g/l with variable ammonium concentrations from 0.3 to 1.3 g/l $NH_4Cl$. With the continuous fermentation, fairly specific production rates from 0 to 0.11 g/gh are obtained with significant isocitric acid formation (3 to 6.5g citric acid/g isocitric acid). In the batch process up to 40 g/l citric acid with isocitric acid is formed while in continuous operation the acid concentration runs up to 14 g/l.

The results given by Klasson et al are not promising for a commercial production since both the total acid concentration and the citrate/isocitrate proportions are unsatisfactory.

OBJECTS OF THE INVENTION

It is therefore an object of the present invention to provide an improved process for the production of citric acid or citrate which can be readily converted to citric acid whereby drawbacks of the earlier processes are avoided.

Another object of this invention is to provide a process for the production of citric acid in the form of citrate which satisfies the need for the commercial requirements.

It is also an object of this invention to provide a commercially acceptable process for the production of citric acid in the form of citrate which gives rise to high citrate concentrations in the outflow of a continuously operated fermenter with high ratios of citrate to isocitrate.

It is a further object of the invention to provide an economical improved process for the production of citric acid as citrate.

SUMMARY OF THE INVENTION

These objects and others which will become apparent hereinafter are attained, in accordance with the invention by providing in the fermentation feed a C/N-ratio corresponding to a ratio of 12 to 22 moles of glucose to moles of ammonium compounds.

Preferably the molar ratio of glucose to ammonium compounds in the feed is maintained at 15 to 18 and the glucose concentration in the feed between 100 and 400 g/l, especially 200 to 300 g/l, with the residence time being between 60 and 120 hours(h).

With this relationship of carbon and nitrogen sources in the feed, surprisingly high concentrations with relatively low isocitrate proportions and high conversion of glucose are obtained with space-time yields in excess of 1.5 g citrate/l h. The invention thus provides in a continuous process a limited formation of biomass which is sufficient however to compensate for washout losses and to renew the biocatalyst.

By contrast with hitherto favored intense aeration and high oxygen concentrations in the fermenter, it is preferred with the present invention to operate in the fermentation with 15 to 30% of air saturation (with reference to the maximum oxygen saturation levels with air under standard conditions, which is lower by a factor of 5as when oxygen is used for the saturation instead of air).

It is especially preferred to maintain 20% air oxygen saturation in the fermenter.

The N limitation dependent upon the residence time is preferably held above the nitrogen minimum concentration required to maintain the viability of the living and producing microorganism. This corresponds to a preferred N concentration in the feed of 50 to 150 mM. The favorable operating conditions had been found to utilize a N concentration of about 0.1M, a residence time in the range of 70 to 90 h and a C concentration corresponding to 300 g/l glucose. The pH value in the fermenter is preferably between 4 and 5.5 (especially between 4.5 and 5.0 and most preferably around 5.0. The presence of traces of iron (in the $\mu$M range) in the fermentation medium shifts the pH optimum to a lower value of about 4.6).

Temperatures betwen 29 and 31° C. are preferred for the fermentation, with 30° C. being most desirable.

It has been found, surprisingly, that the addition of iron ions to the fermenter medium have a significant negative effect, i.e. the best results are obtained by excluding iron from the food.

Zinc and Manganese ions have a positive effect and it has been found that the minimum zinc ion concentration should be 0.05 mM especially about 0.15 mM (for $Zn^{++}$) and about 0.75 mM (for, $Mn^{++}$) which apply for nitrogen contents in the fermenter feed of 3 g/l $NH_4Cl$ and are proportionately higher with increased nitrogen concentrations.

The copper ion concentration is preferably that which corresponds to approximately 2 mg/l copper sulfate while the magnesium ion concentration is in the range of 3 to 5 mM each at N concentrations corresponding to 3 g/l $NH_4Cl$ and proportionately higher with increasing N concentrations in the feed.

Preferably the invention is practiced with yeast without a carrier and without biomass hold back or retention to yield optimum productivity parameters and enable a steady state to be maintained in a continuous manner over long periods of time since the biomass which is washed from the reactor is constantly resupplied by the growth (tough limited). With long residence times, however, we prefer to operate with partial biomass retention (for example 30% depending upon the conditions).

The yeast strains which can be used for the citric acid production according to the invention include:

---
*Candida fibriae*
*C. guilliermondii*
*C. indermedia*
*C. lipolytica*
*C. oleophila*
*C. parapsilosis*
*C. subtropicalis*
*C. tropicalis*
*C. zeylanoides*
--- besides strains of Rhodotorula, Saccharomycopsis or Yarrowia of which the most preferred are *Candida oleophila, Candida lipolytica, Candida tropicalis* and *Candida guilliermondii*. Especially intensive research has been done with respect to the fermentation with the *Candida oleophila* Strain ATCC 20177 with which the data given in the tests described below were obtained.

More particularly, the process for the continuous production of citrate for use in producing citric acid, e.g. by acidification of the citrate, comprises the steps of:

(a) continuously feeding to a fermenter containing a yeast capable of transforming glucose to citric acid by fermentation, in the presence of a nutrient medium and oxygen, a C source like glucose and at least one ammonium compound as an N source;

(b) fermenting the glucose to citric acid in the fermenter at a temperature, a pH and with a residence time sufficient to transform at least a major part of the glucose continuously fed to the fermenter to citric acid;

(c) continuously withdrawing fermentation product from the fermenter;

(d) recovering citrate or citric acid from the fermentation product; and (e) controlling a C/N ratio fed to the fermenter to correspond to a molar ratio of glucose to ammonium compounds of 12 to 22 during fermentation of the glucose to citrate.

Other C sources as saccharose, molasses or hydrolysates of starch which are converted by candida strains for producing citric acid, (being in the culture medium as a mixture of acid and salts all analysed as "citrate" ions) could be used in the inventive process.

BRIEF DESCRIPTION OF THE DRAWING

The above and other objects, features, and advantages will become more readily apparent from the following description, reference being made to the accompanying drawing in which.

FIGS, 1 through 5 are graphs showing the effect of air oxygen saturation on the continuous process for the production of citrate in accordance with the invention.

SPECIFIC DESCRIPTION AND EXAMPLES

The Effect of $O_2$ Saturation in the Fermenter

The curves of FIGS. 1 to 5 show the effect of oxygen saturation upon the continuous citric acid formation (in terms of citrate) with the use of *Candida oleophila* ATCC 20177.

The fermentation was carried out in a 2 l agitator vessel fermenter (Biostat E, Brown & Diesel, Germany) at a pH value of 4.5. The pH value and the oxygen saturation were held constant automatically.

The composition of the fermentation medium is given in Table 1:

TABLE 1

| FERMENTATION MEDIUM | |
|---|---|
| Glucose | 230 g/l |
| $NH_4Cl$ | 4.5 g/l |
| $KH_2PO_4$ | 1.05 g/l |
| $MgSO_4 \cdot 7H_2O$ | 0.525 g/l |
| $CuSO_4 \cdot 5H_2O$ | 1.5 mg/l |
| $Na_2MoO_4 \cdot 7H_2O$ | 300 ug/l |
| $ZnSO_4 \cdot 7H_2O$ | 0.0315 g/l |
| $CoSO_4 \cdot 7H_2O$ | 0.006 g/l |
| $H_3BO_3$ | 0.06 g/l |

TABLE 1-continued

FERMENTATION MEDIUM

| | |
|---|---|
| $MnSO_4 \cdot 1H_2O$ | .25 mM |
| $FeSO_4 \cdot 7H_2O$ | 0 mM |
| $CaCl_2$ | 0.15 g/l |
| NaCl | 0.15 g/l |
| KI | 0.15 mg/l |
| Citric Acid (calculated from citrate ions) | 2.5 g/l |
| Thiaminehydrochloride | 3 mg/l |
| Biotin | 0.375 mg/l |
| Pyridoxinehydrochloride | 0.9375 mg/l |
| Ca-D-Pantothenate | 0.9375 mg/l |
| Nicotinic acid | 0.75 mg/l |
| Temperature | 30° C. |
| pH Value | 4.5 |
| pH-corrector | 45% NaOH-solution |
| Oxygen Saturation | varied with air/$O_2$ mixture |
| Stirrer speed | 600 rpm |
| ($NH_4Cl$ and Vitamin solution | were sterile filtered). |

The investigations were carried out with continuous fermentation in chemostats with different aeration (the percentage oxygen saturation is relative to 100% air oxygen saturation at standard pressure with 1 vvm air and at 1000 rpm in pH 4,5 medium, the corresponding 100% air oxygen saturation in water under the same conditions given in air oxygen saturation in the medium of pH 3.0 of 97% and at pH 4.5 of 98.2%).

Figure 2:
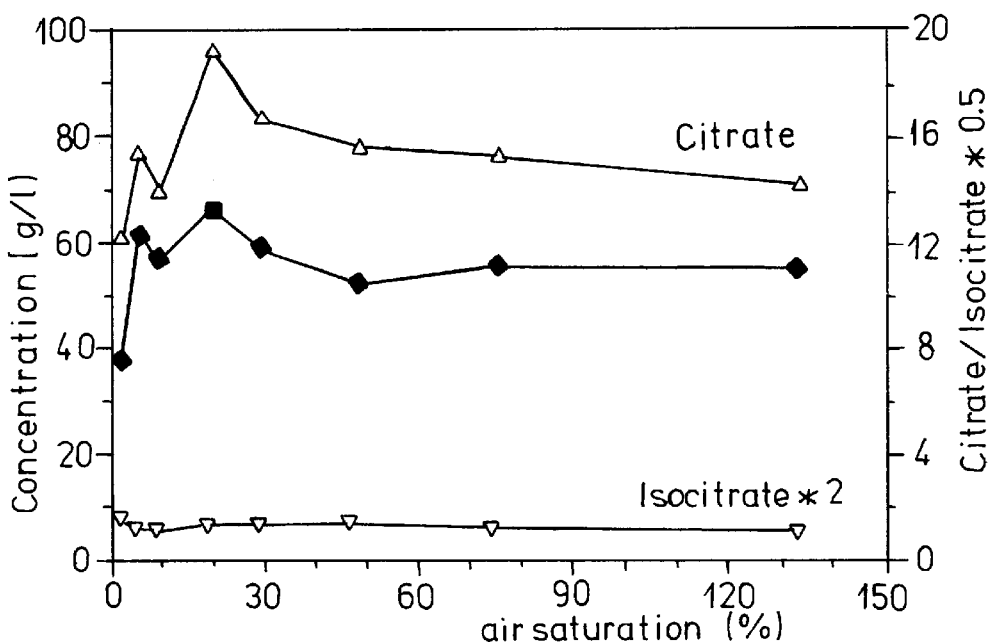

As one can see, the maximum citric acid concentration and the best citrate/isocitrate ratio is obtained at about 20% air oxygen saturation though the isocitric acid concentration falls slightly with increasing air oxygen saturation (see FIG. 2).

Figure 1:
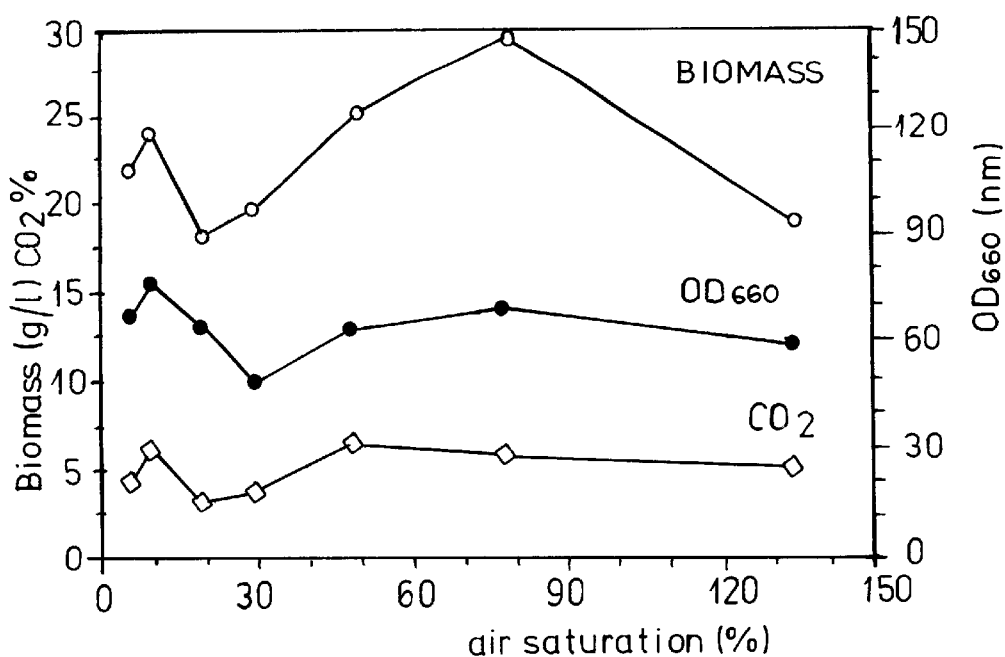

FIG. 1 shows that the biomass formation at 20% air oxygen saturation is reduced, the optical density showing no convincing correlation to the dry biomass.

Figure 3:
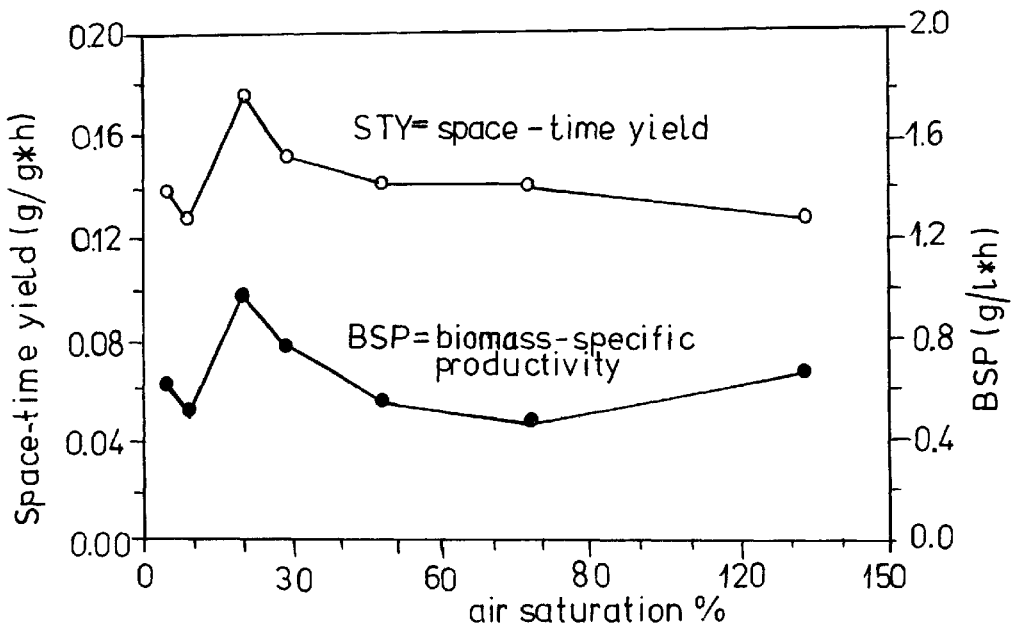

The biomass specific productivity and the space time yield reach their maximum also at 20% air oxygen saturation (see FIG. 3 and the following Table 2).

TABLE 2

Results of the continuous fermentation with 4.5 g/l $NH_4Cl$ and 230 g/l glucose with a residence time of 54.6 H

| Parameter | Value |
|---|---|
| Biomass | 18.085 g/l |
| Citrate | 96.57 g/l |
| Isocitrate | 3.48 g/l |
| Citrate/Isocitrate-ratio | 27.7 |
| Glucose | 74.63 g/l |
| Conversion | 63.77% |
| Yield | 43.95% |
| Saturation | 69.6% |
| Space-Time Yield | 1.77 g Citrate/l*h |
| Specific Productivity | 0.098 g Citrate/g dried biomass*h |

With a residence time of about 54 hours, citric acid can be continuously produced with a selectivity of about 70% with 4.5 g/l $NH_4Cl$ and 20% air oxygen saturation at a rate of 100 g/l citric acid. By prolonging the residence time under otherwise constant fermentation conditions (30° C., pH=4.5, 20% air oxygen saturation and the same fermentation medium) the citric acid concentration and the selectivity are maximized.

Figure 4:
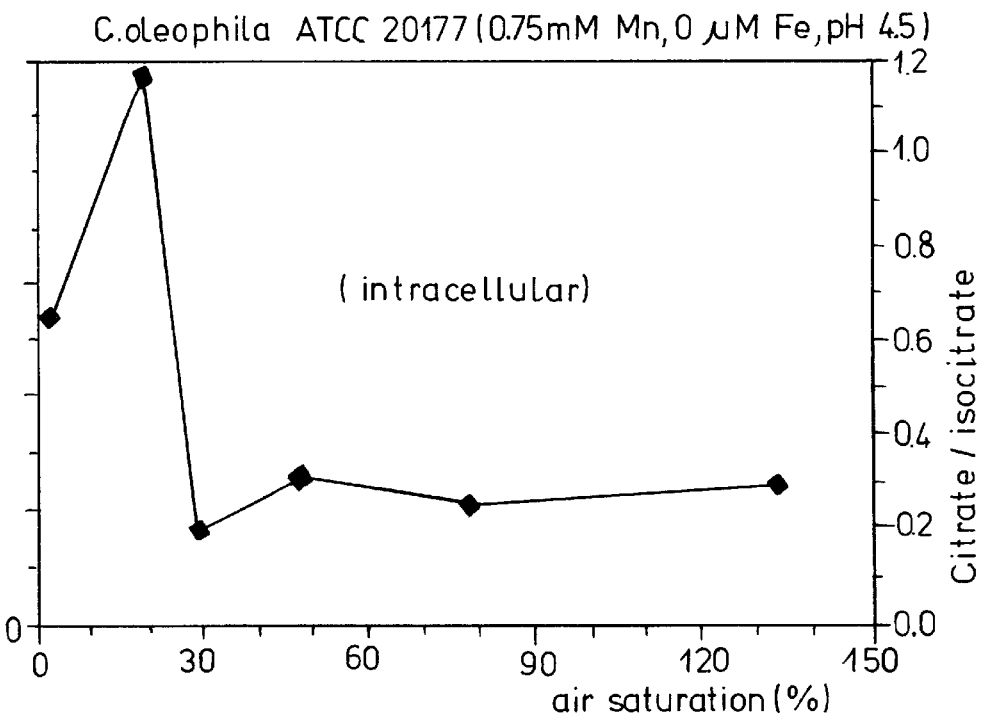
Figure 5:
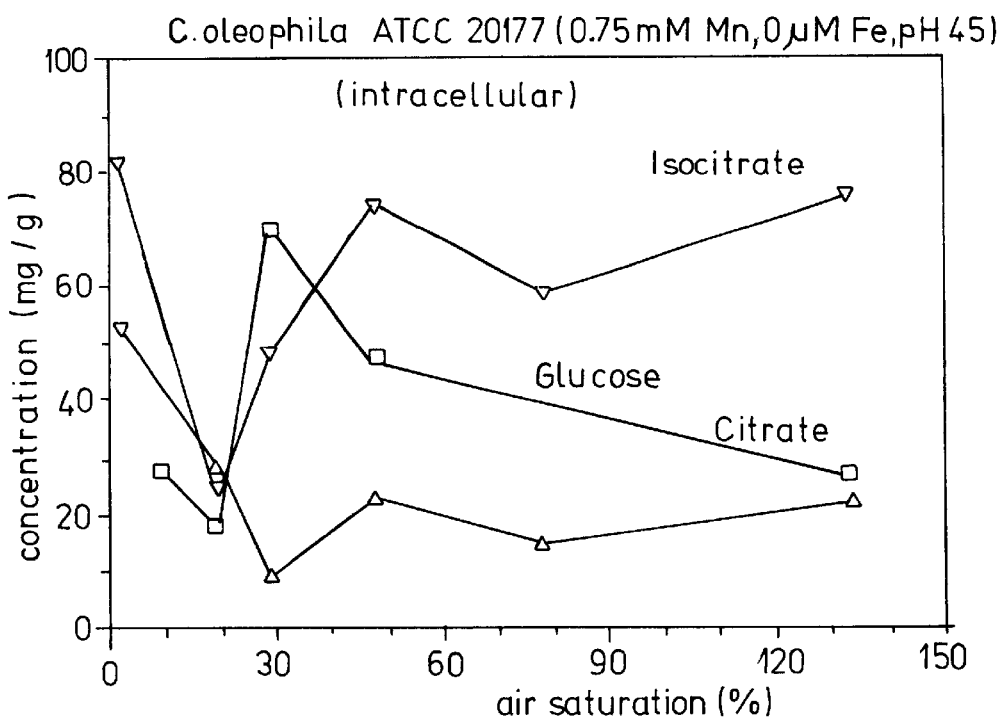
Figure 7:
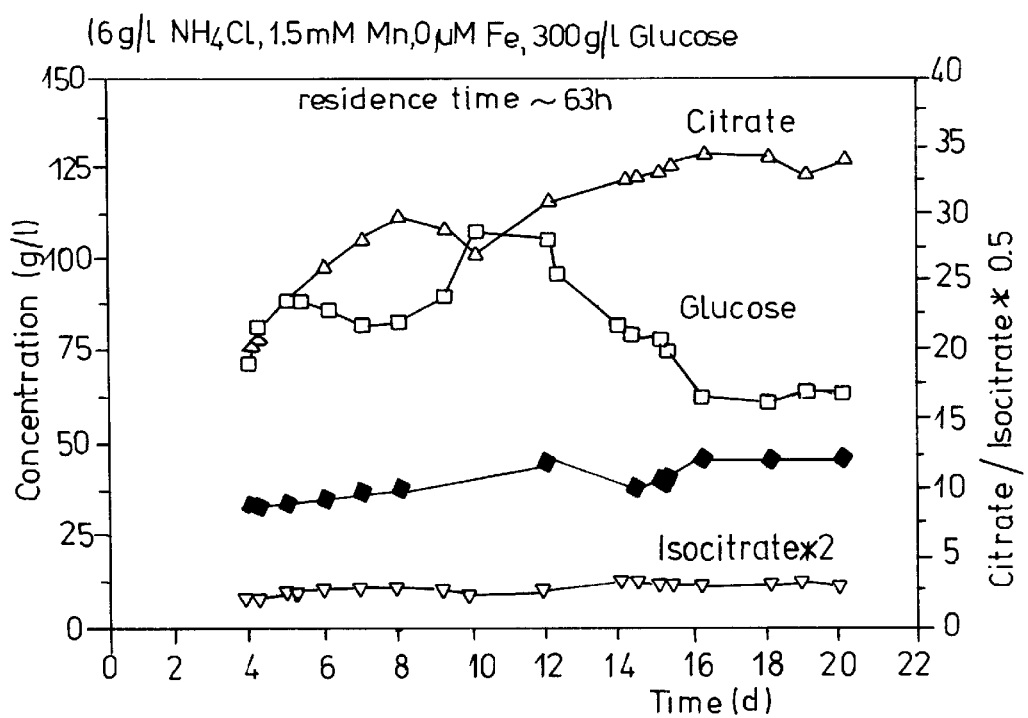

Intracellular concentration measurements show that the intracellular show citrate/isocitrate ratio is significantly lower over the entire range than extracellular as is apparent from FIG. 4. The intracellular isocitric acid concentration, (FIG. 5) with the exception of the region of 20% air oxygen saturation, were higher than the citric acid concentration. This indicates an active highly specific transport system operating preferentially for citric acid. At 20% air oxygen saturation, corresponding to the increased glycolosis rate, the lowest intracellular glucose concentration is measured (FIG. 5).

Effect of the Nitrogen Concentration and the Residence Time

Figure 8:
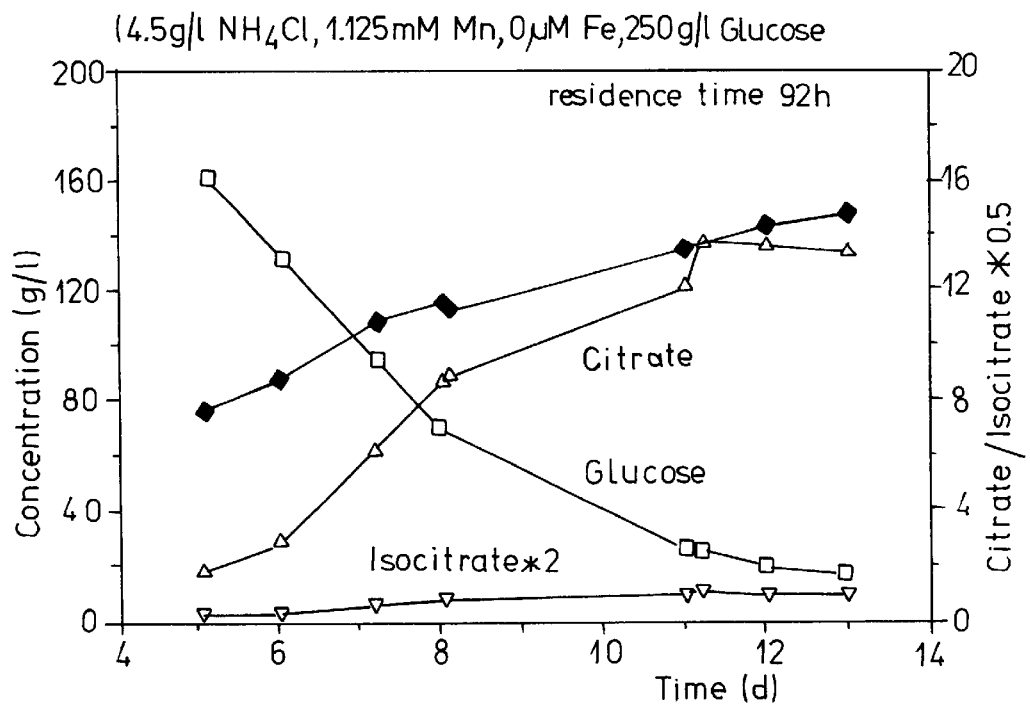
Figure 9:
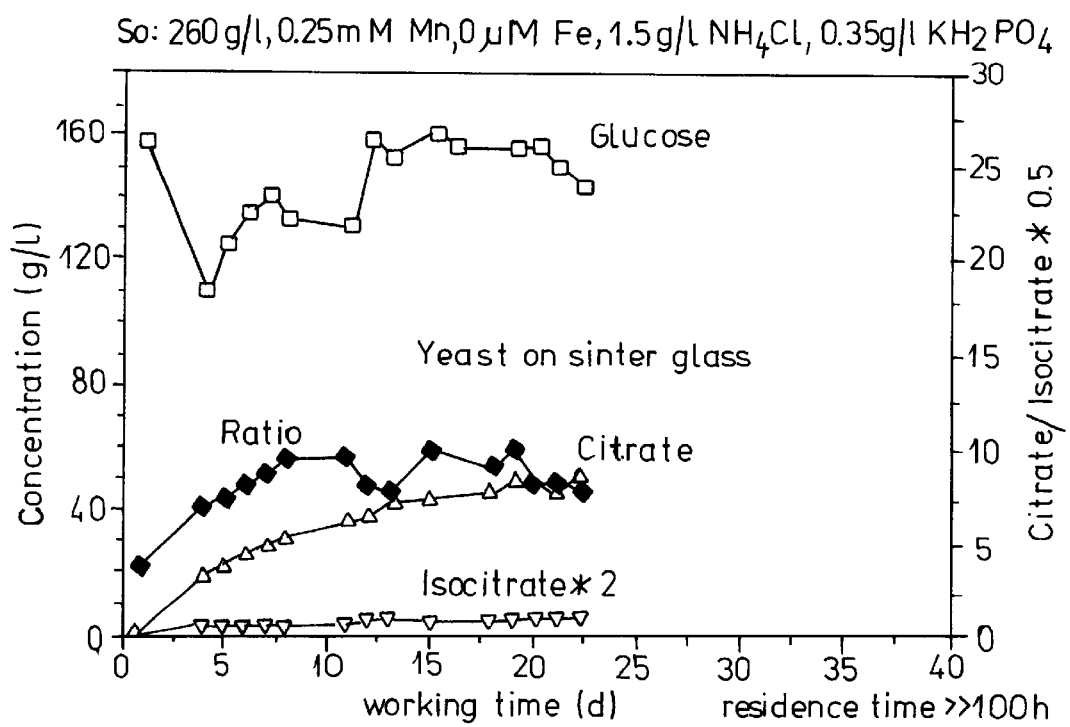
Figure 10:
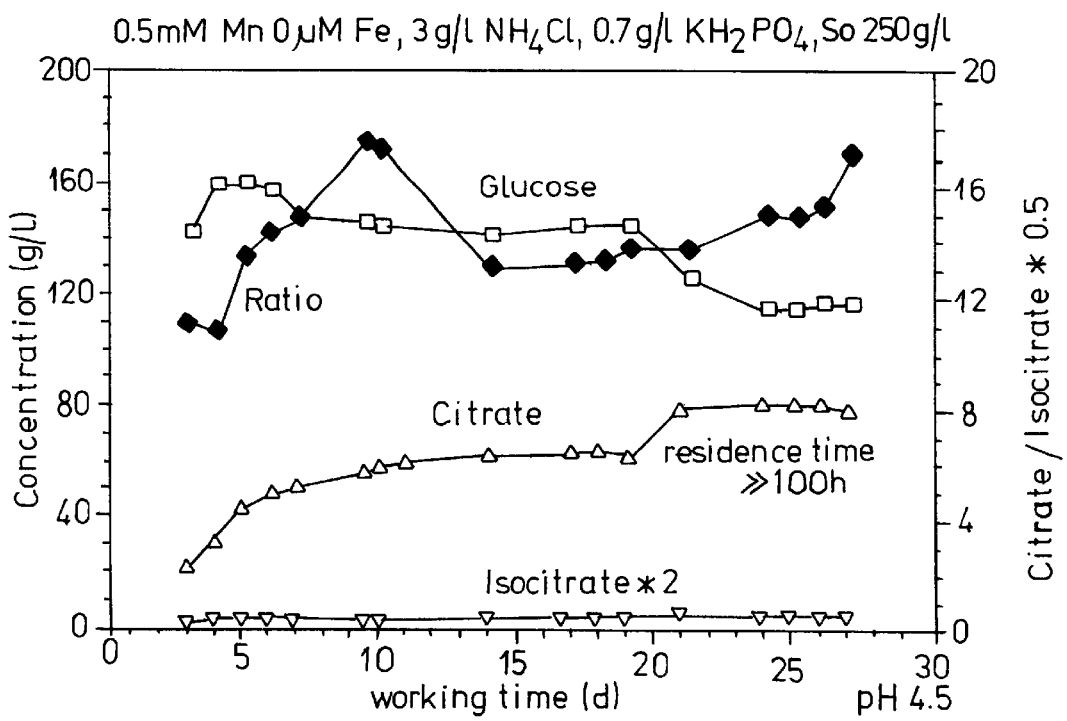

FIGS. 6 to 10 show the dependency of the citrate formation and the citrate isocitrate ratio upon the nitrogen content of the feed and upon the residence time. The medium for the fermentation according to FIG. 9 corresponds to that of Table 3, although with half the concentrations, 260 g/l glucose and the absence of $Fe^{++}$. The operation was carried out with a supported biomass (all of the remaining tests utilizing unsupported yeast and without biomass hold back). FIG. 10 utilized a fermentation medium according to Table 3 but with 250 g/l glucose, without $Fe^{++}$ and with 2 mg/l $CuSO_4 \cdot 5H_2O$.

TABLE 3

Fermentation Medium

| | |
|---|---|
| Glucose | 120 g/l |
| $NH_4Cl$ | 3 g/l |
| $KH_2PO_4$ | 0.7 g/l |
| $MgSO_4 \cdot 7H_2O$ | 0.53 g/l |
| $CuSO_4 \cdot 5H_2O$ | 1 mg/l |
| $Na_2MoO_4 \cdot 2H_2O$ | 200 ug/l |
| $ZnSO_4 \cdot 7H_2O$ | 0.021 g/l |
| $CoSO_4 \cdot 7H_2O$ | 0.004 g/l |
| $H_3BO_3$ | 0.04 g/l |
| $MnSO_4 \cdot 1H_2O$ | 0.5 mM |
| $FeSO_4 \cdot 7H_2O$ | 0.5 mM |
| $CaCl_2$ | 0.1 g/l |
| NaCl | 0.1 g/l |
| KI | 0.1 mg/l |
| Citric Acid | 2.5 g/l |
| Thiaminhydrochloride | 2 mg/l |
| Biotin | 0.25 mg/l |
| Pyridoxinhydrochloride | 0.625 mg/l |
| Ca-D-Pantothenate | 0.625 mg/l |
| Nicotine acid | 0.5 mg/l |
| Temperature | 30° C. |
| pH-Value | 4.5 bzw 5.0 |
| pH-Corrector | 22.5% NaOH |
| (NH Cl and Vitamine solution | were sterile filtered) |
| Aeration rate | 4–5 1/h pure oxygen |
| Magnet stirrer | 900–1300 RPM |

A comparison of FIGS. 9 and 10 shows that with too little nitrogen in the feed in spite of long residence times (>>100 hours) no economically satisfactory citrate formation can be achieved. On the contrary, the commercially effective citrate formation has an optimum nitrogen content such that, with reduced residence times and higher nitrogen concentrations, higher citrate yields are obtained while the glucose conversion and the citrate/isocitrate ratio is somewhat improved with slightly reduced nitrogen content and higher residence times (FIG. 8). In this case the composition of the fermentation medium, apart from the glucose concentration was about 250 g/l, corresponded to that of table 1.

Figure 6:
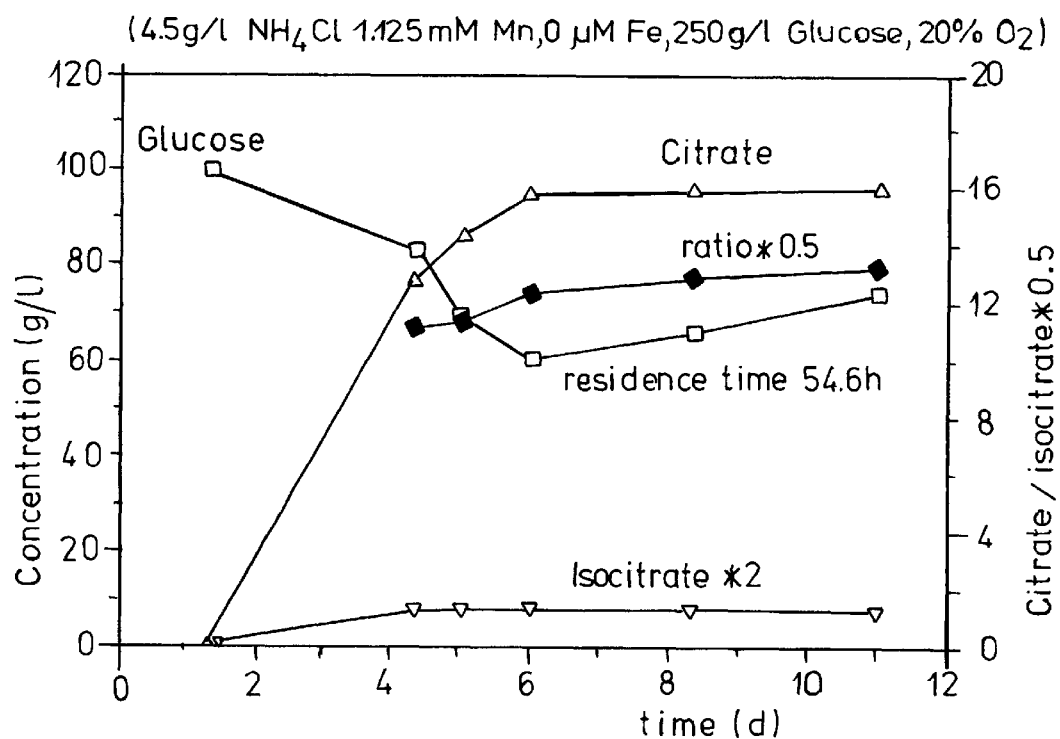
FIGS. 6 through 10 are graphs for the citrate, isocitrate and glucose concentrations in a throughflow fermenter with different residence times and $NH_4Cl$ concentrations in the feed.

With the shortest residence time, there was a lesser utilization of glucose with slightly reduced citrate concentration (FIG. 6). The composition of the fermentation medium corresponded to that of Table 1.

With tests with 6 g/l $NH_4Cl$ (FIG. 7), with residence times of about 63 hours, about 130 g/l citric acid (in terms of citrate) could be obtained. In this case, the space time yield amounted to 2 g/l.h. The fermentation medium used is set out in Table 4.

TABLE 4

Fermentation medium for continuous fermentation with 6 g/l NH$_4$Cl and 300 g/l glucose at a residence time of 63 hours.

| | |
|---|---|
| Glucose | 300 g/l |
| NH$_4$Cl | 6 g/l |
| KH$_2$PO$_4$ | 1.4 g/l |
| MgSO$_4$.7H$_2$O | 0.7 g/l |
| CuSO$_4$.5H$_2$O | 3 mg/l |
| Na$_2$MoO$_4$.2H$_2$O | 400 ug/l |
| ZnSO$_4$.7H$_2$O | 0.02 g/l |
| CoSO$_4$.7H$_2$O | 0.008 g/l |
| H$_3$BO$_3$ | 0.08 g/l |
| MnSO$_4$.1H$_2$O | 1.5 mM |
| FeSO$_4$.7H$_2$O | 0 mM |
| CaCl$_2$ | 0.2 g/l |
| NaCl | 0.2 g/l |
| KI | 0.2 mg/l |
| Citric Acid | 2.5 g/l |
| Thiaminehydrochloride | 4 mg/l |
| Biotin | 0.5 mg/l |
| Pyridoxinehydrochloride | 1.25 mg/l |
| Ca-D-Pantothenate | 1.25 mg/l |
| Nicotine acid | 1 mg/l |
| Temperature | 30° C. |
| pH-Value | 4.5 |
| pH-Corrector (NH$_4$Cl and Vitamine solution were sterile filtered) | 45% NaOH-soltion |
| Air Saturation | 20% |
| Mixer speed | 600 rpm |

Table 5 shows the results obtained in this fermentation:

TABLE 5

Results of the continuous fermentation with 6 g/l NH$_4$Cl and 300 g/l glucose with a residence time of 63 hours.

| Parameter | Value |
|---|---|
| Biomass | 25.895 g/l |
| Citrate | 127.06 g/l |
| Isocitrate | 4.98 g/l |
| Citrate/Isocitrate-ratio | 25.5 |
| Glucose | 63.12 g/l |
| Conversion | 76.32% |
| Yield | 44.68% |
| Saturation | 68.35% |
| Space-Time Yield | 2.01 g Citrate/l*h |
| Specific Productivity | 0.076 g Citrate/g dried biomass*h |

In the optimization of the nutrient medium components, a medium with 3 g/l NH$_4$Cl and 120 g/l or 180 g/l glucose was used. The tests were carried out in a double jacketed glass small fermentor with a total volume of 1000 ml.

To effect the mixing, the fermenter was set on a magnetic stirrer utilizing a stirrer capsule in the reaction vessel. The oxygen supply was insured utilizing pure oxygen to better simulate oxygen supply to a commercial size agitated fermenter.

The substrate and the sodium hydroxide solution were supplied by peristaltic pumps from 5 and 20 liter supply flasks, respectively, A simple riser tube or overflow insured the constant volume of the fermentation medium in the vessel.

The feed substrate concentration was corrected for dilution of the medium in the vessel by the sodium hydroxide solution pumped into the latter to correct the pH.

From the sum of the amount of substrate and the pumped in sodium hydroxide solution per unit time and based upon the working volume of the reactor, residence time was calculated. To reach steady state as a rule 5 to 10 residence times were required. The biomass concentration, the optical density, the characteristic of citrate/isocitrate and the nitrogen concentrations were analyzed.

All fermentations were carried out at 30° C. and at pH 4.5 with the exclusion of the manganese or iron optimization experimentations (which were carried out at a pH of 5.0). Table 3 shows the starting medium for the optimization of the continuous citric acid fermentation with *Candida oleophila* ATCC 20177 after each optimization the optimal value was selected for the subsequent optimization.

pH Effect

The influence of the pH at 30° C and a residence time of about 40 hours with 120 g/l glucose and 3 g/l NH$_4$Cl was determined in chemostats. A medium analysis to that of Table 3 was used with 5 μm iron (I).

In tests without iron the medium was analogous to that of Table 1 with 250 g/l glucose and 3 mg/l copper sulfate (II).

TABLE 6

Fermentation Medium I

Analogous to Table 3

| | |
|---|---|
| MnSO$_4$ · 1H$_2$O | 0.5 mM |
| FeSO$_4$ · 7H$_2$O | 5 μM |
| Temperature | 30° C. |
| pH-Value | 2.0 bis 6.0 |
| pH-Corrector | 22.5% NaOH-solution |
| Aeration rate | 4–5 1/h pure oxygen |
| Magnet stirrer | 1300 RPM |

TABLE 7

Fermentation Medium II

Analogous to Table 1

| | |
|---|---|
| MnSO$_4$ · 1H$_2$O | 1.125 mM |
| FeSO$_4$ · 7H$_2$O | 0 μM |
| Temperature | 30° C. |
| pH-Value | 4.0 bis 6.0 |
| pH-Corrector | 22.5% NaOH-solution |
| Aeration rate | 4–5 1/h pure oxygen |
| Magnet stirrer | 900 RPM |

Figure 11:
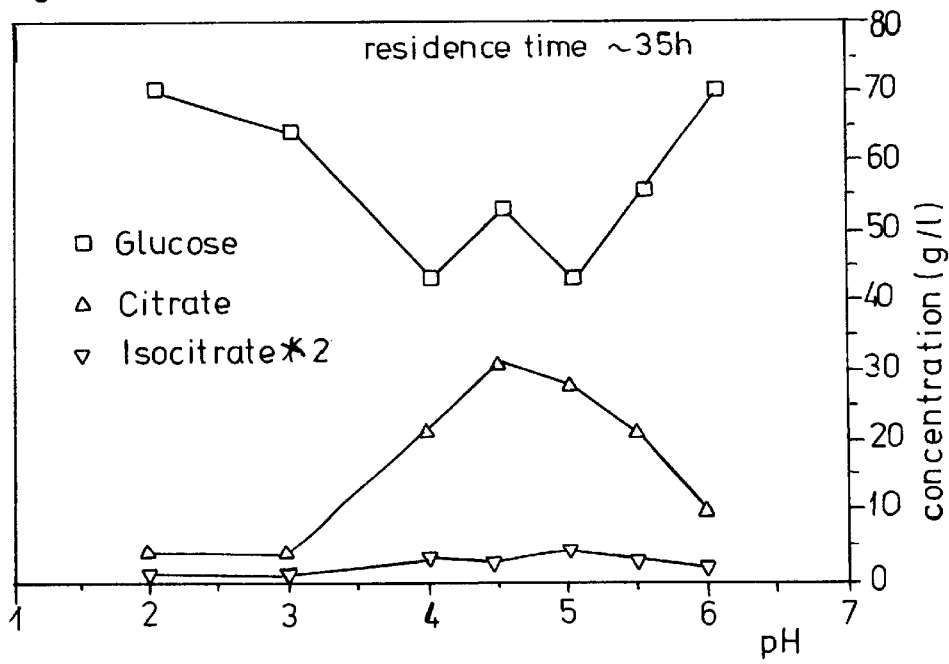
FIGS. 11 and 12 are graphs showing the effect of the pH value.
Figure 12:
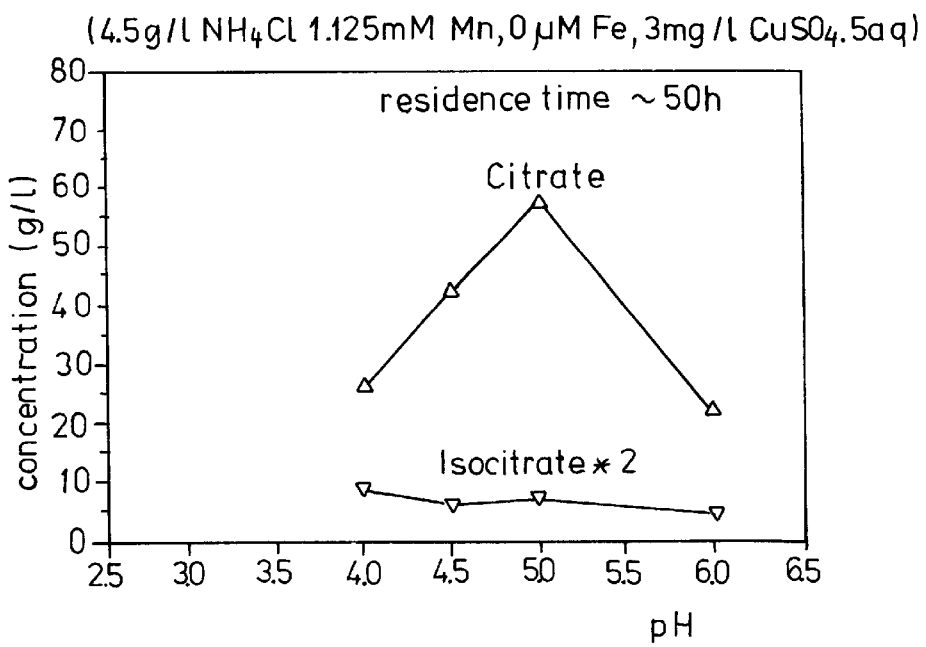

FIGS. 11 and 12 show the effect of pH value on the product formation. An increase of the pH value from 2 to 4 results in a clear reduction in glucose and increase in the citrate/isocitrate ratio and the citrate concentration (FIG. 11). As FIG. 11 shows, an optimum citrate formation in the range of pH 4 to 5 is observed which shifts, as further experiments have indicated, in the absence of iron to higher values. With reduced iron proportion, the optimum lies closer to 4.5 and without reduction in the iron proportion the optimum lies closer to 5.0. This dependency has been shown with a reduced residence time of about 35 hours.

Influence of Iron

A medium analogous to that of Table 3 was used with varying iron concentrations between 20 μM and 1000 μM (1 mM).

TABLE 8

Fermentation Medium

Analogous to Table 3

| | |
|---|---|
| $FeSO_4 \cdot 7H_2O$ | 20–1000 $\mu M$ |
| Temperature | 30° C. |
| pH-Value | 5.0 |
| pH-Corrector | 22.5% NaOH-solution |
| Aeration rate | 4–5 1/h pure oxygen |
| Magnet stirrer | 900 RPM |

Figure 13:
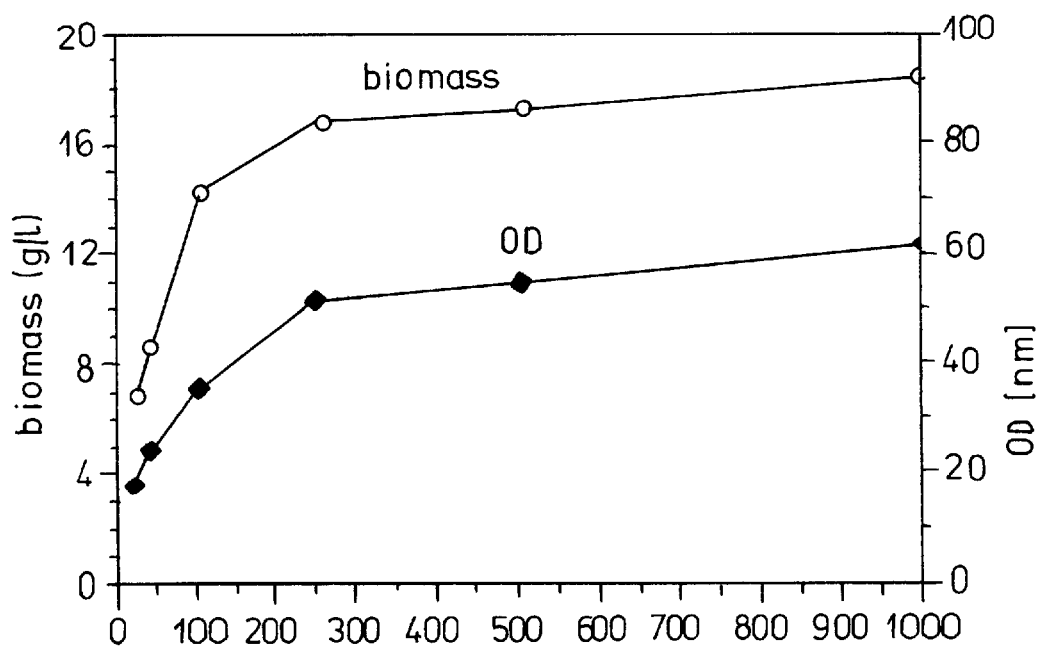
FIGS. 13 to 15 are graphs showing the influence of iron upon the biomass formation and product recovery, respectively.
Figure 14:
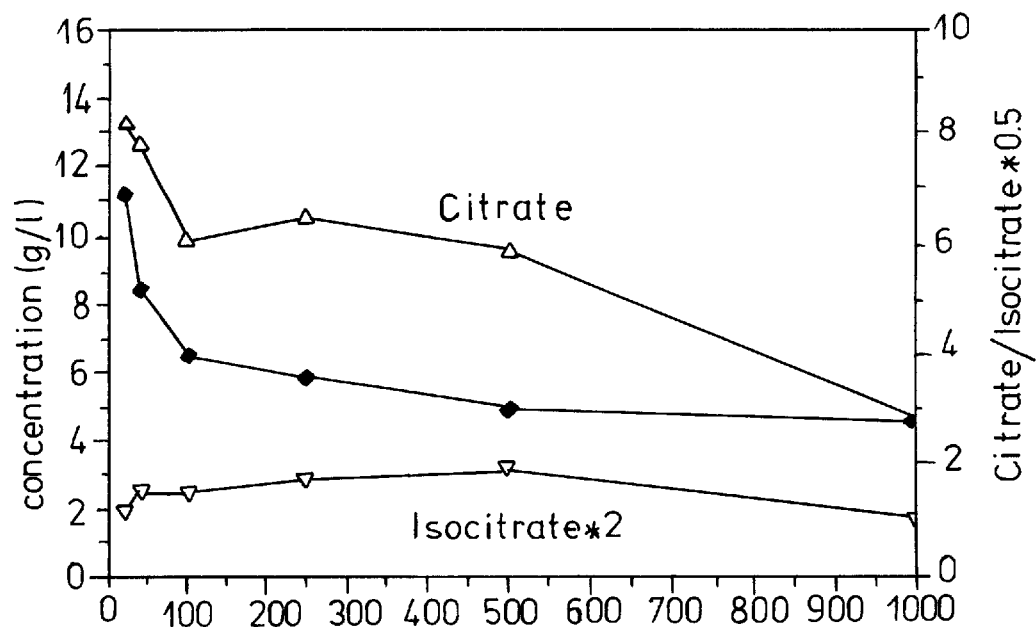
Figure 15:
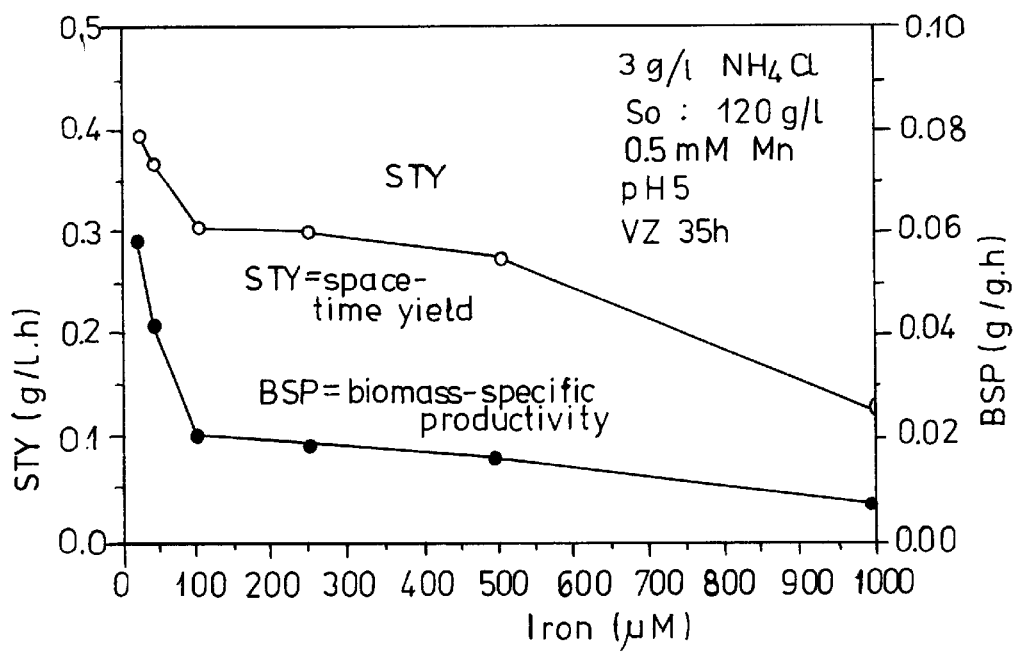

FIGS. 13 through 15 clearly show that with increasing iron content there is an increased growth of the biomass although the citrate formation is reduced even with a minor iron content. The same applies for the citrate/isocitrate ratio and the space time yield and specific productivity (FIGS. 14 and 15).

Effect of Temperature

TABLE 9

Fermentation Medium

Analogous to Table 3

| | |
|---|---|
| Glucose | 180 g/l |
| $CuSO_4 \cdot 5H_2O$ | 2 mg/l |
| $MnSO_4 \cdot 1H_2O$ | 0.75 mM |
| $FeSO_4 \cdot 7H_2O$ | 0 $\mu M$ |
| Temperature | 30° C. |
| pH-value | 4.5 |
| PH-Corrector | 22.5% NaOH-solution |
| Aeration rate | 4–5 1/h pure oxygen |
| Magnet stirrer | 900 RPM |

Figure 16:
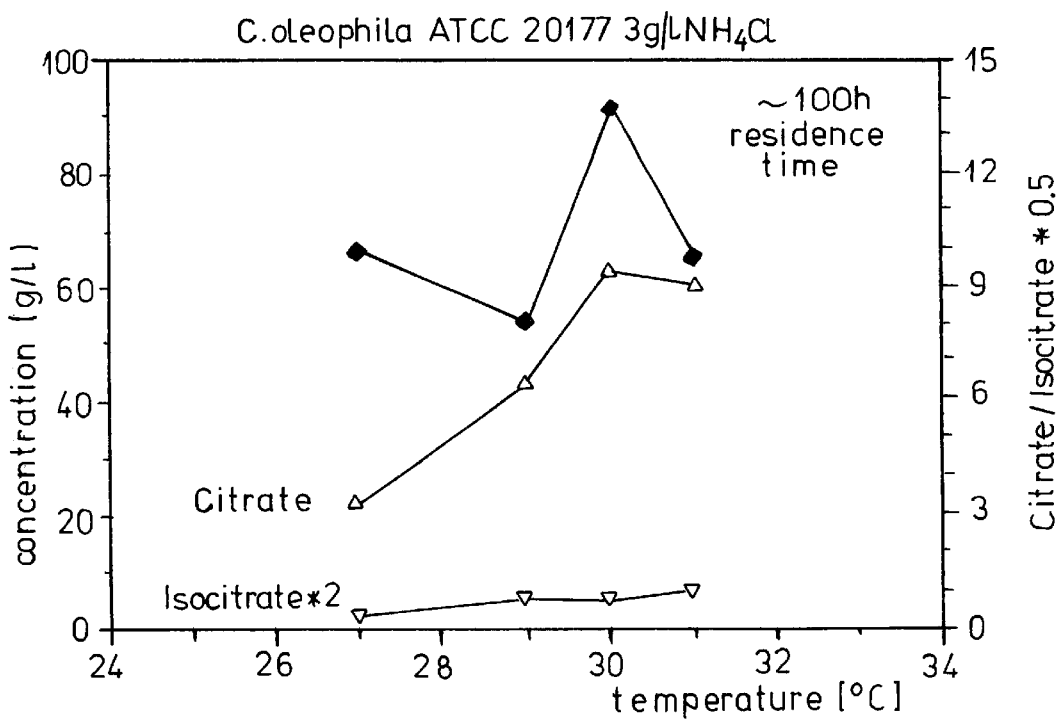
FIG. 16 is a graph showing the influence of temperature upon the citrate and isocitrate formation.

FIG. 16 shows that the system is sensitive to the effective temperature and that both citrate formation and the citrate/isocitrate ratio are influenced. An optimum is found at 30° C.

Influence of Zinc Ions

Figure 17:
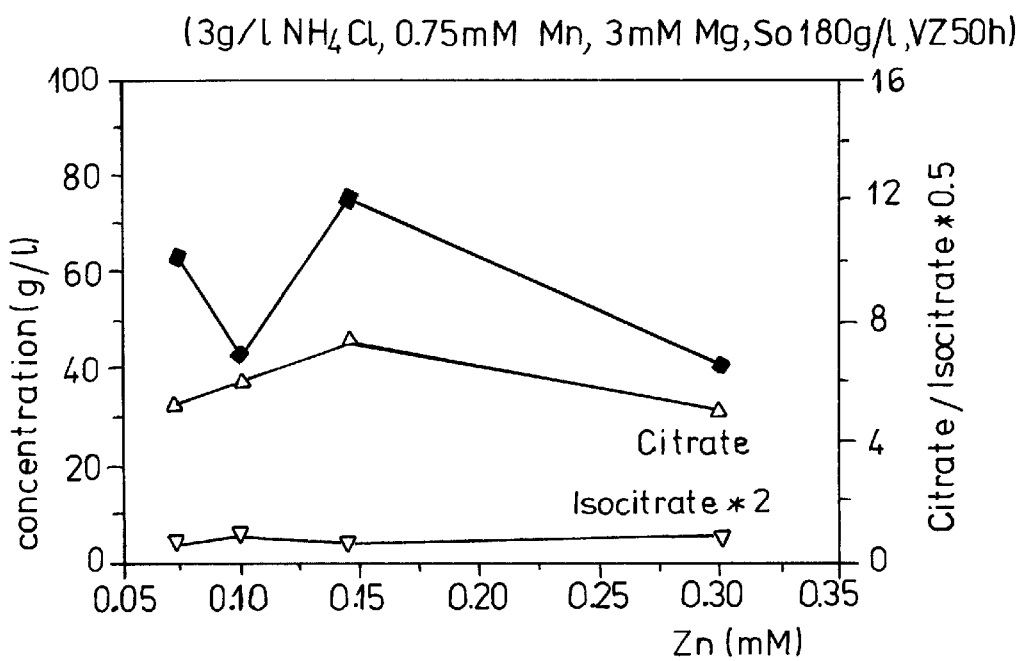
FIGS. 17 and 18 are graphs showing the influence of zinc upon the processes.
Figure 18:
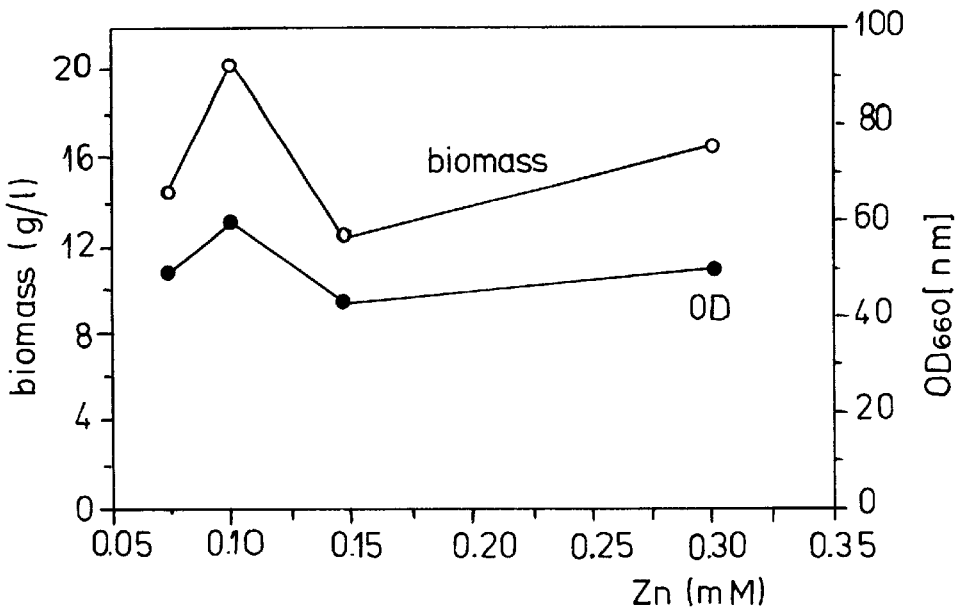

The effect of zinc ions is shown in FIGS. 17 and 18. The zinc ions clearly have a significant effect on the citrate concentration and the citrate/isocitrate ratio which does not correlate with the biomass and optical density in the fermenter. Preferably the $Zn^{++}$ concentration should be 0.15 mM at 3 g/l $NH_4Cl$ although the preferred zinc concentration varies with n concentration. The composition of the fermentation medium corresponded here was to that of TABLE 3 but with 0.75 mM $Mn^{++}$, 3 mM $Mg^{++}$, 2 mg/l $CuSO_{4.} 5H_2O$ and exclusion of $Fe^{++}$ ions.

The following Table 10 represents a Summary of the tests results with different glucose and $NH_4Cl$ concentrations in the feed and different residence times with otherwise identical or similar conditions.

TABLE 10

The isocitrate concentrations and the citrate/isocitrate rations shown in the diagrams are to be multiplied by a factor of 0.5 or 2 respectively.

| Parameters | Units Value | | | | | | | |
|---|---|---|---|---|---|---|---|---|
| $NH_4Cl$ | g/l | 3 | 4.5 | 4.5 | 6 | 6 | 6 | 7.5 |
| Glucose | g/l | 250 | 250 | 350 | 300 | 350 | 400 | 400 |
| Glucose/$NH_4Cl$ | g/g | 83 | 55.6 | 77.8 | 50 | 58.3 | 66.7 | 53.3 |
| residence time | h | 100 | 54.6 | 68.2 | 63 | 75.7 | 79 | 79 |
| Biomass | g/l | 12 | 18.1 | 18.1 | 25.9 | 28 | 30.7 | 37.5 |
| Citrate | g/l | 82 | 98 | 105.7 | 127.1 | 126.6 | 125 | 143.5 |
| Isocitrate | g/l | 3.3 | 2.95 | 3.8 | 5 | 5.53 | 5.7 | 8.5 |
| Citrate/Isocitrate | — | 25 | 33.3 | 27.8 | 25.5 | 22.9 | 22 | 17 |
| Glucose Conversion | % | 47 | 63.8 | 51.2 | 76.3 | 80.8 | 78.2 | 100 |
| Yield | g/l | 118 | 74.6 | 154.8 | 63.1 | 60.2 | 75.7 | 0 |
| | % | 33 | 44 | 28 | 44.7 | 40.6 | 36.1 | 46 |
| Selectivity | % | ~72 | 69.5 | 54.6 | 68.4 | 50.3 | 46.1 | 46 |
| Space-Time Yield | g Citrate/(1*h) | 0.82 | 1.77 | 1.55 | 1.95 | 1.67 | 1.58 | 1.82 |
| BSP* | g Citrate/(g*h) | 0.07 | 0.098 | 0.086 | 0.076 | 0.06 | 0.052 | 0.048 |

In each case, following recovery of the citrate solution from the fermenter, the solution could be acidified for recovery of citric acid utilizing conventional techniques.

*"BSP" means "biomass specific productivity"

We claim:

1. A process for the continuous production of citrate or citric acid, comprising the steps of:
   (a) continuously feeding to a fermenter containing a yeast of the genus Candida capable of transforming glucose to citric acid by fermentation and a nutrient medium, oxygen, a carbon source selected from the group consisting of glucose, saccharose, molasses and hydrolysates of starch which are convertible by candida strains to citric acid, and at least one ammonium compound as a nitrogen source, to obtain a fermentation medium containing the carbon source in a concentration corresponding to 200 to 400 g/l of glucose;
   (b) fermenting the carbon source in the fermentation medium to citric acid in said fermenter at a temperature of about 29 to 31° C; a pH of 4 to 5.5 and for a mean residence time of 60 to 120 hours, while controlling the carbon/nitrogen ratio of the carbon source and the nitrogen source fed to said fermenter to correspond to a molar ratio of 12 to 22 parts carbon source taken as glucose per part nitrogen source, taken as $NH_3$, and controlling an oxygen concentration in said fermenter to correspond to 15 to 30% of air oxygen saturation of said medium;
   (c) continuously withdrawing fermentation product from said fermenter; and
   (d) recovering citrate or citric acid from said fermentation product.

2. The process of claim 1 wherein the molar ratio of glucose to ammonium compounds fed to said fermenter is 15 to 18 and the glucose concentration in said fermentation medium is 200 to 300 g/l.

3. The process of claim 1 wherein said oxygen concentration in said fermenter is controlled to correspond to about 20% of air oxygen saturation of said medium.

4. The process of claim 1 wherein a minimum concentration of the nitrogen source above that required for sustaining viable and productive microorganisms in said fermentation medium, is maintained in said fermentation medium.

5. The process of claim 4 wherein a nitrogen source concentration in said fermentation medium is maintained at 50 to 150 mM.

6. The process of claim 5 wherein said nitrogen source concentration in said fermentation medium is maintained at about 0.1M, said residence time is 70 to 90 h, and said carbon source has a concentration in said fermentation medium corresponding to about 300 g/l.

7. The process of claim 1 wherein said pH is about 4.5 to 5.0.

8. The process of claim 1, further comprising the step of excluding iron from the fermentation medium in said fermenter.

9. The process of claim 1, further comprising the step of operating said fermenter at a pH of about 4.6 upon detection of traces of iron in said medium in a $\mu$M range.

10. The process of claim 1, further comprising the step of maintaining in said fermentation medium a nitrogen source dependent zinc ion concentration of $\geq 0.05$ mM, a manganese ion concentration of about 0.75 mM, a copper ion concentration corresponding to about 6 to 8 $\mu$M of copper sulfate and a magnesium ion concentration of 3 to 5 mM at a nitrogen source concentration in said nutrient medium corresponding to 3 g/l $NH_4Cl$ and proportionally higher with higher nitrogen source concentrations.

11. The process of claim 10 wherein said zinc ion concentration is about 0.15 mM.

12. The process of claim 2 wherein said fermenter is operated as a throughflow fermenter without biomass retention and with unsupported yeast.

13. The process of claim 12 wherein:

said yeast is selected from the group which consists of:
   Candida fibriae
   Candida guilliermondii
   Candida indermedia
   Candida lipolytica
   Candida oleophila
   Candida parapsilosis
   Candida subtropicalis
   Candida tropicalis and
   Candida zeylanoides;

a nitrogen source concentration in said fermentation is maintained at 50 to 150 mM;

and said fermentation broth is controlled to maintain a nitrogen source dependent zinc ion concentration of $\geq 0.05$ mM, a manganese ion concentration of about 0.75 mM, a copper ion concentration corresponding to about 6 to 8 $\mu$M of copper sulfate and a magnesium ion concentration of 3 to 5 mM at a nitrogen source concentration in said fermentation broth corresponding to 3 g/l $NH_4Cl$ and proportionally higher with higher nitrogen source concentrations.

14. The process of claim 13 wherein said zinc ion concentration is about 0.15 mM.

15. The process of claim 14 wherein said pH is 4.5 to 5.0.

\* \* \* \* \*